United States Patent [19]
Arnett et al.

[11] Patent Number: 5,464,390
[45] Date of Patent: Nov. 7, 1995

[54] SURGICAL MULTIORIFICE IRRIGATION APPARATUS

[75] Inventors: Jeffrey D. Arnett, Kalamazoo; David H. Grulke, Battle Creek, both of Mich.

[73] Assignee: Stryker Corporation, Kalamazoo, Mich.

[21] Appl. No.: 158,526

[22] Filed: Nov. 29, 1993

[51] Int. Cl.$^6$ .................................................. B05B 1/34
[52] U.S. Cl. ............................ 604/35; 604/275; 15/320
[58] Field of Search ................................ 604/27, 28, 30, 604/35, 39, 43, 275, 289, 310, 902; 606/131; 239/488, 501, 504, 520, 552; 15/320, 321, 322

[56] References Cited

U.S. PATENT DOCUMENTS

| | | | |
|---|---|---|---|
| 487,655 | 12/1892 | Wardell | 604/39 |
| 611,454 | 9/1898 | Longden | 604/275 |
| 688,688 | 12/1901 | Pumphrey | 604/275 |
| 1,017,638 | 2/1912 | McCoole | 239/552 |
| 2,839,052 | 6/1958 | Verch et al. | 604/289 |
| 3,049,303 | 8/1962 | Kocher | 239/488 |
| 3,640,472 | 2/1972 | Hruby, Jr. et al. | 239/552 |
| 3,692,245 | 9/1972 | Needham et al. | 239/488 |
| 3,797,755 | 3/1974 | Saisho | 239/552 |
| 4,692,140 | 9/1987 | Olson | 604/35 |
| 4,904,238 | 2/1990 | Williams | 604/35 |
| 5,046,486 | 9/1991 | Grulke et al. | 128/66 |
| 5,269,750 | 12/1993 | Grulke et al. | 604/21 |

FOREIGN PATENT DOCUMENTS 1377120  2/1988  U.S.S.R. .................................. 604/28

OTHER PUBLICATIONS

Copy of Stryker Brochure No. 4500 001 121 JJB, dated Dec. 1988 which in the lower left photo shows several alternative Excel (TM) tips (including the 207–110 Excel Multi Orifice Tip) (1 page).
Copy of P. 24 of Davol/Bard Brochure, which drawings identify several of their tips, including Model Nos. 3760, 3773, 3771, etc (1 page) (no date).
Copy of Zimmer Brochure–Pulsavac Wound Debridement System and assorted irrigation outlet tips, including Model 5150–81 and Model 5150–85 (1 page) (no date).

Primary Examiner—Stephen C. Pellegrino
Assistant Examiner—Nancy Mulcare
Attorney, Agent, or Firm—Flynn, Thiel, Boutell & Tanis

[57] ABSTRACT

A tip member is to be fixed adjacent the distal end of the irrigation outlet tube of a surgical irrigation handpiece. The tip member modifies the irrigation liquid flow to direct same forwardly toward a surgical site as multiple, narrow, discrete streams of irrigation liquid. Such streams have length axes which are skewed with respect to each other, so as to cross each other in laterally spaced relation. Such streams angle away from the central axis of the irrigation tube. Such angled, pulsed streams can more easily be directed at an acute angle to a surgical site.

22 Claims, 4 Drawing Sheets

SURGICAL MULTIORIFICE IRRIGATION APPARATUS

FIELD OF THE INVENTION

This invention relates to surgical irrigation apparatus and particularly to a wand for a surgical suction-irrigation handpiece.

BACKGROUND OF THE INVENTION

Grulke et al U.S. Pat. No. 5,046,486, assigned to the assignee of the present invention, discloses a suction-irrigation handpiece including a forward extending, elongate wand comprising irrigation and suction tubes, through which, respectively, a pulsed irrigation liquid is applied to a surgical site and flowable materials are suctioned from the surgical site. This device has been marketed by the present assignee, Stryker Corporation, of Kalamazoo, Mich., under the trademark EXCEL.

The EXCEL (TM) device has been sold with a straight cylindrical irrigation outlet flow port. In addition the EXCEL (TM) device has been sold with a modified tip member in which the irrigation outlet flow path is blocked by a coaxially close spaced pair of radially extending disks each having four, evenly circumferentially spaced, axial through holes. The forward disk is angularly offset through 45°, about the common axis of the two disks, with respect to the rearward disk, so that irrigation flow through the holes in the first disk hits the forward disk between the holes therein, filling the space between the disks with a circumferentially turbulent mass of irrigation liquid, from which liquid eventually escapes through the circumferentially offset holes in the forward disk. The result is a substantially solid cross-sectional flow of conical profile, forward from the forward disk or, in other words, a substantially solid, forwardly travelling, radially diverging, solid stream. With such tip member used with the EXCEL (TM) handpiece, such stream is axially broken into a series of axially substantially discrete, generally disk-like slugs, or pulses. This tip member tends to reduce the force of impact of each liquid pulse on the surgical site, and spread same over a larger area, and substantially reduces the irrigation liquid flow rate to the surgical site (substantially reduces the irrigation liquid delivered per unit time at the surgical site).

The present assignee also markets an improved pulsed irrigation-suction handpiece, capable of more forceful, sharply defined, irrigation liquid pulses, under the trademark SURGILAV PLUS.

In both of the above-mentioned suction-irrigation handpieces, the suction and irrigation tubes are coaxially telescoped and form a removable wand which extends forward from the housing of the handpiece. The irrigation liquid tube is of lesser diameter than, and is coaxially disposed within the larger diameter suction tube. The tubes are radially fixed one within the other, with an annular suction passage radially between the two, by structure at the proximal and distal ends of the tubes. The structure at the distal ends of the tubes comprises circumferentially spaced, radially extending fins extending radially outward from the distal end of the irrigation tube to engage the interior surface of the suction tube. The handpiece is actuable by a surgeon, or surgical assistant, to forcibly forwardly expel pulses of irrigation liquid from the distal end of the irrigation tube and to suction a flowable material from the surgical site, into the distal end of the suction tube and thus into the annular space surrounding the irrigation tube.

The SURGILAV PLUS (TM) device is capable of unusually forceful, sharply defined irrigation liquid pulses and is thus particularly effective for difficult surgical site cleaning jobs wherein unwanted bits of tissue or the like may be difficult to remove from surfaces at the surgical site. For example, the SURGILAV PLUS (TM) device has been found particularly effective in cleaning bits of soft tissue out of a femoral cavity in preparation for cementing therein of the elongate, ball-supporting stem of a hip joint prothesis.

However, the present Applicant has noted that use of the same suction-irrigation handpiece for medical/surgical procedures with substantially different requirements (for example in terms of force and pattern of irrigation liquid output from the handpiece), would help limit increase of medical costs to the public, for example by limiting the number of different types of suction-irrigation handpieces needed to be designed, manufactured and inventoried by suppliers and bought and inventoried by medical practitioners.

Applicant has further noted that it is in some instances desirable to use multiple, narrow, discrete streams of irrigation liquid pulses to tissue at the full force capability of the handpiece, e.g. the SURGILAV PLUS (TM) handpiece. Such streams have length axes which are skewed with respect to each other, so as to cross each other in laterally spaced relation. Such streams angle away from the central axis of the irrigation tube. Such angled, pulsed streams can more easily be directed at an acute angle to a surgical site surface without having to angle the irrigation tube and handpiece. Such angled, pulsed streams also can dislodge debris from a surgical site surface by a kind of chiseling action, i.e. by digging laterally under debris and prying it off the surgical site surface. An example is the cleaning of debris from the tibial plateau in knee surgery. However, Applicant notes that it is desirable to avoid reduction in flow rate (unit volume per unit time) of irrigation liquid to the surgical site.

Accordingly, the objects and purposes of the present invention include provision of a tip member for a surgical irrigation wand for varying the nature of irrigation liquid flow from an irrigation handpiece, particularly to adapt to multipoint angled cleaning of surgical sites.

SUMMARY OF THE INVENTION

A tip member is to be fixed adjacent the distal end of the irrigation outlet tube of a surgical irrigation handpiece. The tip member modifies the irrigation liquid flow to direct same forwardly toward a surgical site as multiple, narrow, discrete streams of irrigation liquid. Such streams have length axes which are skewed with respect to each other, so as to cross each other in laterally spaced relation. Such streams angle away from the central axis of the irrigation tube. Such angled, pulsed streams can more easily be directed at an acute angle to a surgical site.

Other objects and purposes of the invention will be apparent to persons acquainted with apparatus of this type upon reading the following description and inspecting the accompanying drawings.

BRIEF DESCRIPTION OF THE DRAWINGS

FIG. 1 is a schematic view of a suction irrigation handpiece having a forwardly extending, preferably removable and replaceable, suction-irrigation wand including a tip member embodying the invention, the showing of the wand being fragmentary.

FIG. 2 is an enlarged fragmentary pictorial view of the

3 distal (forward) end of the FIG. 1 wand, including a schematic representation of the irrigation liquid outflow pattern from the FIG. 1 tip member.

FIG. 3 is an enlarged, fragmentary, partially broken, exploded, pictorial view of the FIG. 2 structure, taken generally from the front.

DETAILED DESCRIPTION

The present invention may be practiced in connection with a handpiece 10. The handpiece 10 schematically shown in FIG. 1 may, for example, be of a kind marketed by Stryker Corporation under the trademark SURGILAV PLUS (TM), and disclosed in copending U.S. application Ser. No. 08/049 144 (attorney reference Stryker Case 130), assigned to the assignee of the present invention. Such a handpiece 10 includes a substantially pistol-shaped housing 11 comprising a forward extending barrel 12 and a hand engageable handle 13 depending from the rear portion of the barrel 12. A motor M, for example an electric motor M, fixedly mounted in the handle 13 drives, by any convenient means schematically indicated in FIG. 1, a pump P for irrigation liquid, which pump is located in the barrel 12.

An elongate flow directing wand 20 extends forward from the barrel 12 and preferably is releasably fixable thereto, as schematically indicated at 21.

Figures 1, 2, 3:
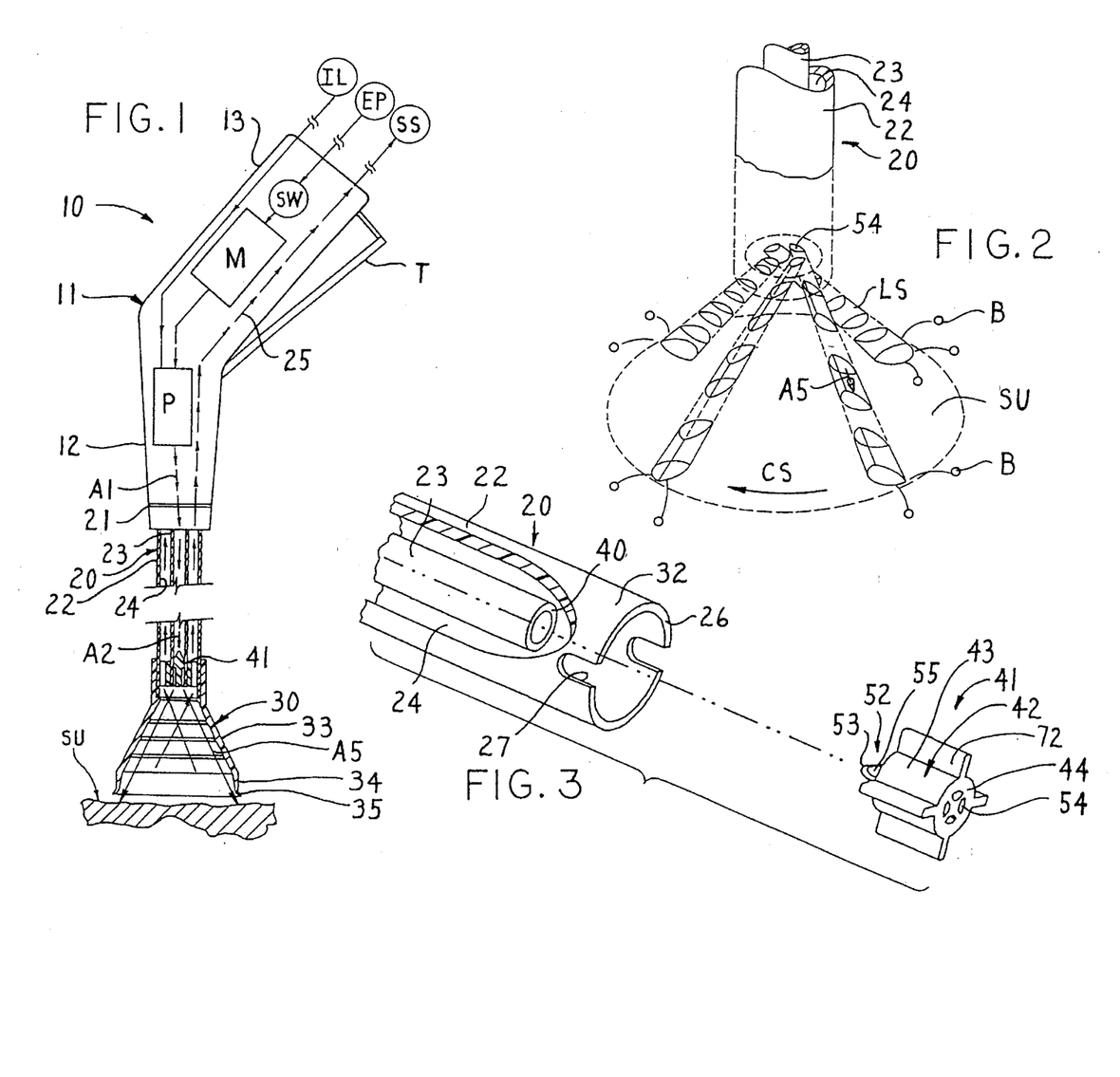
Figure 4:
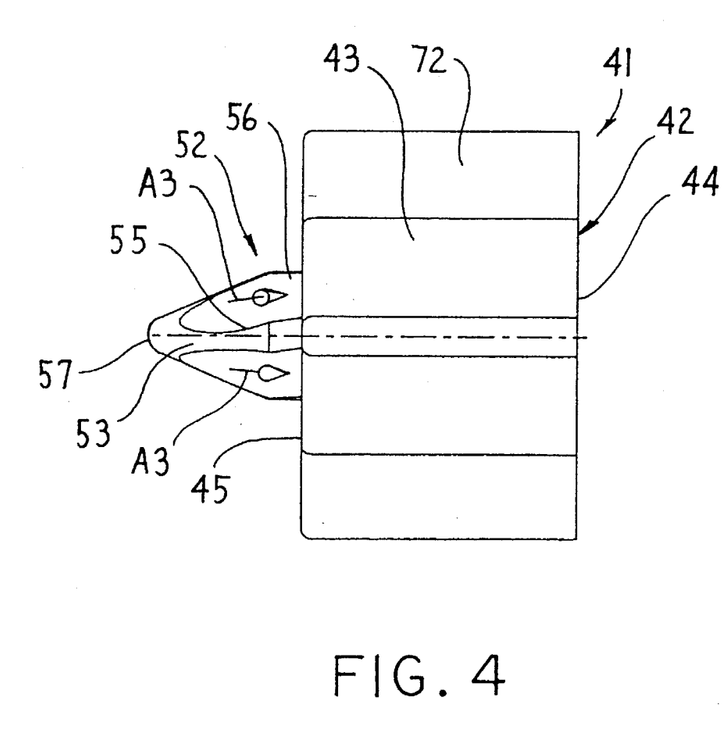
FIG. 4 is an enlarged side elevational view of the FIG. 3 tip member.
Figure 5:
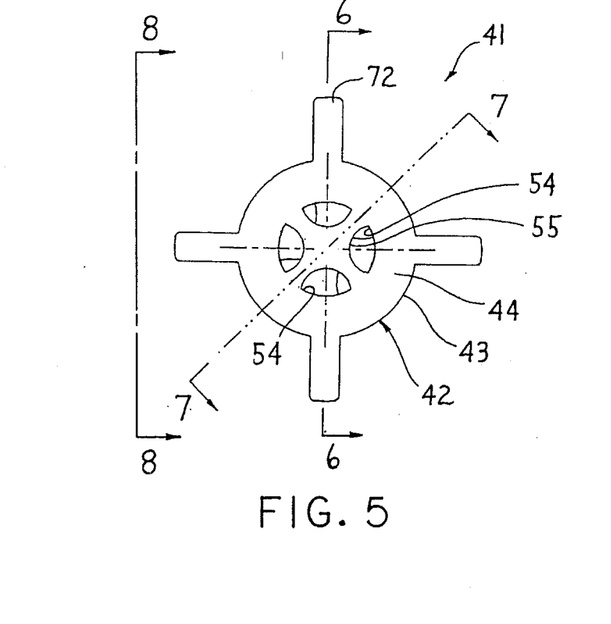
FIG. 5 is an enlarged front view of the FIG. 3 tip member.

The wand 20 comprises an outer suction tube 22 loosely and coaxially surrounding an inner irrigation tube 23 and thereby defining an annular suction passage 24 radially therebetween. As schematically indicated in FIG. 1, the motor M is energizable through a switch SW from a suitable power source, for example an electric power source EP, by manual actuation of a trigger T to actuate switch SW. The pump P is supplied with irrigation liquid from an irrigation liquid source IL and supplies irrigation liquid pulses to the irrigation tube 23 in response to actuation of the motor M.

The suction tube 22 connects through a suitable passage, schematically indicated by the arrows 25 in FIG. 1, with a suction source SS in a conventional manner. The handpiece 10 may or may not be equipped with a manual control for turning on and off suction to the suction tube 22, as in the EXCEL (TM) device or SURGILAV PLUS (TM) device, respectively, above described.

The distal end 26 of the suction tube 22 may for example be provided with front opening notches 27 (FIG. 3) to facilitate passage of flowable materials from a surgical site SU into the suction tube 22 if the distal end 26 of the suction tube 22 is brought close to the surface of the surgical site.

While the present invention was developed with handpieces of the type as schematically disclosed with FIG. 1 in mind, it will be understood that the present invention is useable with medical irrigation apparatus of other kinds, for example non-suction handpieces, steady stream rather than pulsed irrigation output sources, different means to pressurize the irrigation liquid, and so forth.

In the unit shown in FIG. 1, a funnel-shaped spray shield 30 extends divergently forward from the distal end 26 of the suction tube 22. As shown in more detail in FIG. 6, the funnel-shaped spray shield 30 has a cylindrical proximal neck 31 frictionally sleeved over the distal end portion 32 of the suction tube 22. The neck 31 of the spray shield can easily be slid on to and off of the distal end portion 32 of the suction tube 22 as desired, such that the suction tube 22 can be used with or without the spray shield as the surgeon prefers. The spray shield 30 has a frustroconical bell 33 (FIG. 1) which extends divergently forwardly from the suction tube 22. A forward rim 34 at the front end of the bell 33 here terminates an axially short, forward flaring and feathering lip 35. The lip 35 can be brought close to (as in FIG. 1), or into actual contact with, the surface of the surgical site SU, to reduce or eliminate sideward splashing of irrigation liquid as it hits the surface of the surgical site SU and thereby protect surgical personnel from splashing liquid.

The proximal (rear) end portion of the irrigation tube 23 is fixed, by means not shown, preferably coaxially, in the area of the releasable connection 21, with respect to the suction tube 22. The front (distal) end of the irrigation tube 23 is fixed, preferably coaxially, with respect to the distal end portion 32 of the suction tube 22.

To the extent above described, the apparatus is available on the market, for example as the above-mentioned apparatus sold under the trademark SURGILAV PLUS by Stryker Corporation of Kalamazoo, Mich., the present assignee.

Turning now to aspects of the disclosed apparatus more closely related to the present invention, the distal end portion 40 (FIG. 6) of the irrigation tube 23 terminates behind the distal end 26 of the suction tube 22 and is located coaxially within the suction tube 22 by support of a tip member 41 (FIGS. 3–7). The tip unit 41 is preferably a rigid, one-piece member of molded plastics material, for example, a modified acrylic, such as CYROLITE (TM) available from Cyro Industries located at Mt. Arlington, N.J.

The tip member comprises an elongate body 42 having a preferably circular, cylindrical, outer perimeter surface 43 (FIG. 3) terminating forwardly in a distal end wall 44 having a substantially planar distal end face preferably perpendicular to the central axis of the tip member and of the tubes 22 and 23 with which it is associated. The tip member body 42 further comprises a proximal (rear) end 45 (FIGS. 6 and 7) having a deep, central, coaxial, proximally opening and preferably circularly cylindrical recess 46 for snugly but slidably receiving the distal end portion 40 (FIG. 6) of the irrigation tube 23 therein. Thus, in the manner shown in FIG. 6, the tip member 41 is rearwardly sleeveable over the front end of the irrigation tube. The tip member 41 is thus telescoped over and extends slightly forwardly from the irrigation tube in coaxial alignment therewith. The tip member 41 may be fixed on the front end of the irrigation tube 23 by any convenient means, such as adhesive bonding. When thus installed, the distal end 50 of the irrigation tube 23 abuts, or comes close to abutting, the rear facing end wall 51 of the recess 46.

An axially elongate, central, coaxial core 52 (FIGS. 6 and 7) is integral with and extends rearwardly (leftwardly in FIG. 6) from the axially narrow distal end wall 44 for forwardly diverging the flow of irrigation liquid therealong. The core 52 is thus rearwardly fixedly cantilevered from the distal end wall 44. The core 52 is coaxial with the recess 46 and its tapered, generally conical rear end portion 53 is offset rearward substantially beyond the end 45 (FIG. 7) of the body 42. The rear end of the conical rear end portion 53 forms a rounded nose 57 (FIG. 6).

An array of plural (preferably four), evenly circumferentially spaced passages 54 spirals axially and circumferentially through the tip member 41, from adjacent the nose 57 forwardly through the distal end wall 44, to open forwardly through the latter. Each passage 54 here spirals circumferentially through about 45° angle from axial end to end. The array of passages 54 coaxially surrounds the core 52. The passages 54 define grooves 55 in the core 52 (FIGS. 5 and 6), circumferentially separated by lands 56 and radially outwardly opening into the recess 46. The nose 57 of the core 52 is spaced radially inboard from, and hence is ungrooved by, the passages 54.

It will be noted that the diameter of the interior bore 73 (FIG. 10) of the irrigation tube 23 is less than that of an imaginary circle closely bounding imaginary circles 74 continuing the cross section of the radially inner contour of the passages 54 (i.e. of the grooves 55). Indeed, the outside diameter (FIG. 10) of the irrigation tube 23 closely bounds the outside of such imaginary circles 74.

Figure 6:
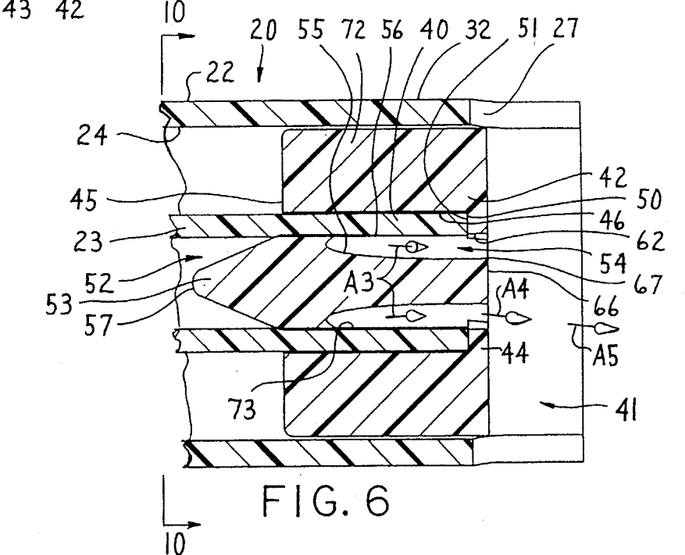
FIG. 6 is a fragmentary, enlarged central cross sectional view substantially taken on the line 6—6 of FIG. 5.
Figure 7:
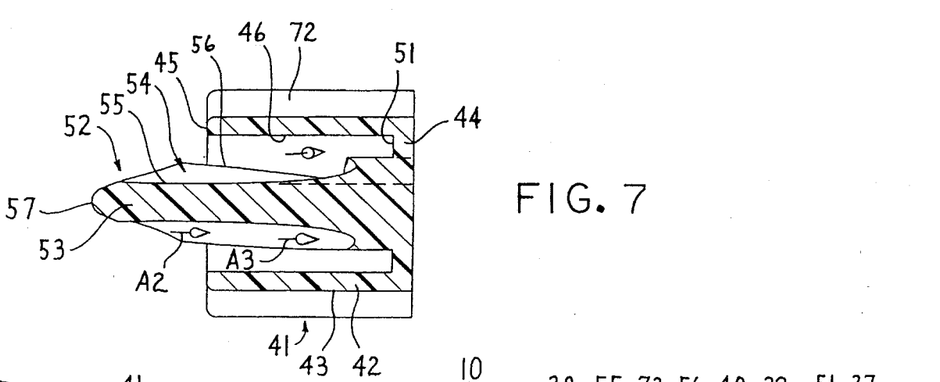
FIG. 7 is a central cross-sectional view of the tip member taken on the line 7–7 of FIG. 5.
Figure 8:
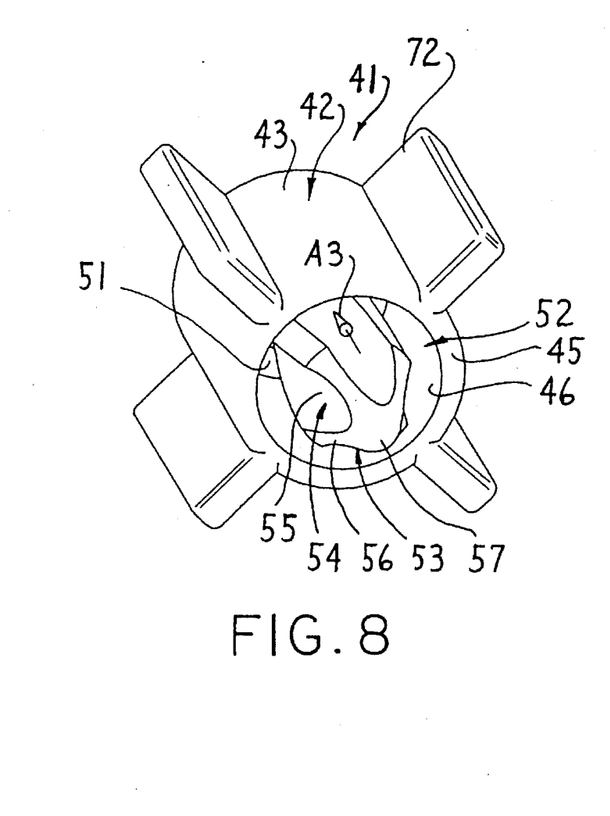
FIG. 8 is an enlarged pictorial view of the FIG. 3 tip member taken generally from the rear end thereof.
Figure 10:
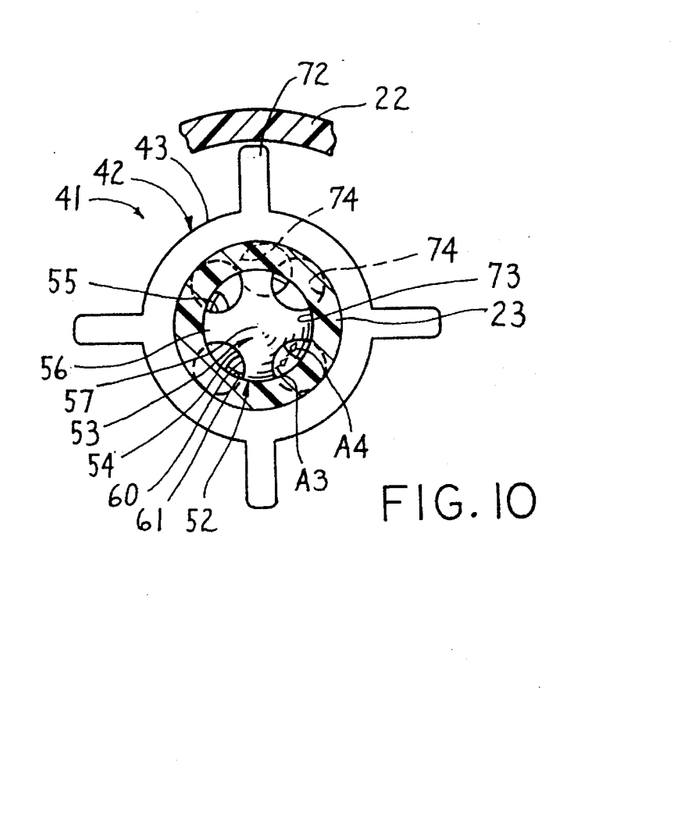
FIG. 10 is a rear end view substantially taken on the line 10—10 of FIG. 6.

The irrigation tube 23 when inserted in the recess 46, as shown in FIGS. 6 and 10, fills in the radially outer portion of the imaginary circles 74 and instead itself defines the radially outer extent of the passages 54. As a result, the cross section of each passage 54 is shaped generally like the profile of an asymmetrical football, wherein the cross section of each passage 54 has a more sharply rounded radially inner portion 60 and a less rounded (flatter) radially outer portion 61 (FIG. 10). Holes 62 axially through the end wall 44 are located and sized and shaped to forwardly continue the passages 54 forwardly through the distal end wall 44.

The included angles, in the plane of the paper, described by (1) the tapered rear end 53 of the core 52 and the inside wall of the frustoconical bell 33 of the spray shield 30, in the embodiment shown, are about (1) 46° and (2) 56° respectively.

The core 52 and passages 54 thus skew the irrigation liquid flow as it flows forwardly therepast. The sharpness of the perimeter edge 67 (FIG. 6) at the forward end of each passage 54 minimizes the tendency of the forward irrigation flow to bend radially and flare and become turbulent in front of the tip member 41, and instead helps the skewed flow separate cleanly from the tip member forward end wall 66. The skewed irrigation flow streams continuing forward out through the spray shield 30 have, as generally indicated by the arrows A5 in FIG. 1, a somewhat lesser angle of divergence than the spray shield 30 itself so that the flow does not tend to significantly impact, or adhere to, the interior surface of the bell 33 and lip 35 of the spray shield 30. The irrigation liquid flows forward from the tip member 41 thus defines plural (here four), skewed streams (pulsed as generally indicated in FIG. 2) of forward moving liquid.

Plural, preferably four, evenly circumferentially spaced fins 72 (FIGS. 3–7) extend along and radially out from the outer perimeter surface 43 of the body 42. As seen in FIG. 3, the fins 72 are each substantially rectangular in a longitudinal/radial plane. The fins 72 are substantially equal in radial extent to center the body 42 and irrigation tube 23 in the suction tube 22. The fins 72 (FIGS. 4 and 6) here extend substantially the length of the body 42 and contact the suction tube 22 to steady the body 42 and irrigation tube 23 within the suction tube 22.

OPERATION

The tip member 41 is preferably molded in one piece. For example, the recess 46 (FIG. 7) and core 52, with its spiral grooves at 55, can be formed by a rearwardly removable inner mold member in the shape of a right circular cylindrical shell (for forming the recess 46), provided on its interior surface with helically extending ribs (for defining the grooves 55), and having a closed rear end wall with a forwardly facing coaxial concavity (for forming the rounded nose 57). Upon completion of molding and curing, such mold part can be removed from the formed tip member 41 by twisting and pulling rearward of the mold member from the tip member 41 to, in effect, unthread the mold member from the tip member 41. The outside of the tip member 41 is conveniently formed by an outer mold member having a cylindrical bore (for forming the outside, perimeter surface 43 of the tip member 41) and having axially and radially extending, circumferentially spaced deep grooves (for forming the fins 72) and having a closed, forward, flat end wall (for forming the front face of the distal end wall 44 of the tip member 41). It is convenient for the body 42 to carry four evenly circumferentially spaced (at 90° circumferential separation) fins 72 and grooves 55.

The tip member 41 can be fixed to the distal end of the irrigation tube 23 prior to insertion of the irrigation tube 23 into the suction tube 22, during assembly of the wand 20. The fins 72 are an axially sliding fit within the suction tube 22. The wand 20 may be permanently affixed to the handpiece barrel 12, but is preferably releasably connected thereto by the known (e.g. EXCEL (TM) or SURGILAV PLUS (TM)) releasable connection schematically indicated at 21, to allow use alternatively of different wands, for example provided with different tip members 41, with the same handpiece 10. Similarly, a given wand 20 can be used with or without the removable spray shield. Indeed, during surgery, different wands 20 can be interchanged preferably on the same handpiece 10 and a spray shield 30 can be placed on or removed from the wand 20 to be used.

In operation, the handpiece 10 is conventionally connected to the irrigation liquid source IL, electric power source EP and suction source SS, as schematically indicated in FIG. 1. Actuation of the switch SW, by hand actuation of the trigger T, energizes the motor M from the electrical power source EP, to activate the pulsing pump P, which draws irrigation liquid from the irrigation liquid source IL and outputs a series of irrigation liquid pulses through the irrigation tube 23 and tip member 41, toward the area of the surgical site surface SU to be cleaned.

At the same time, flowable material, such as expelled irrigation liquid and bits of patient tissue entrained therein, is drawn into the distal end of the suction tube 22 past the fins 72 of, and along the outer perimeter surface 43 of, the tip member 41, thence rearward along the annular suction passage 24 (FIG. 1) between the suction and irrigation tubes 22 and 23, and thence along the suction path schematically indicated at 25 in the handpiece, to the suction source SS. The fins 72, the tip member outer perimeter surface 43 and the interior surface of the suction tube 22 act together, as a sort of four hole screen, to limit the size of solid particles to be drawn into the annular suction passage 24.

It will be noted that the tip member 41 is somewhat axially recessed within the suction tube 22 so that the forwardmost portion of the tip member is spaced slightly rearward from the front end of the suction tube 22. Thus, even with the spray shield 30 removed from the suction tube 22, the distal end of the suction tube can be brought into contact with a given surface, such as the surgical site surface SU, without physical contact of the surface SU with the tip member 41. At the same time, however, the tip member 41 is close enough to the front end of the suction tube 22 that irrigation liquid flow forward out of the passages 54 can diverge, as caused by the tip member 41, without significant constraint by the front end of the suction tube 22 (and indeed without significant constraint by the spray shield 30 when the latter is in place on the front end of the suction tube).

Attention is now specifically directed to the pattern of irrigation flow. The particular handpiece 10 here shown for purposes of illustration of environment, forwards irrigation liquid to the irrigation tube 23 in a series of pulses. The above-mentioned SURGILAV PLUS (TM) device is for example capable of about 1200 irrigation liquid pulses per minute outputted past the tip member 41, with a force of about 0.4 to 0.6 Newtons, and a flow rate of about 900 milliliters per minute, although substantial variations up and down from those numbers are contemplated. In any event, irrigation liquid flow forward from the pump P is schematically indicated by the arrows A1, A2, A3, A4, A5 in FIGS. 1 and 6.

Figure 9:
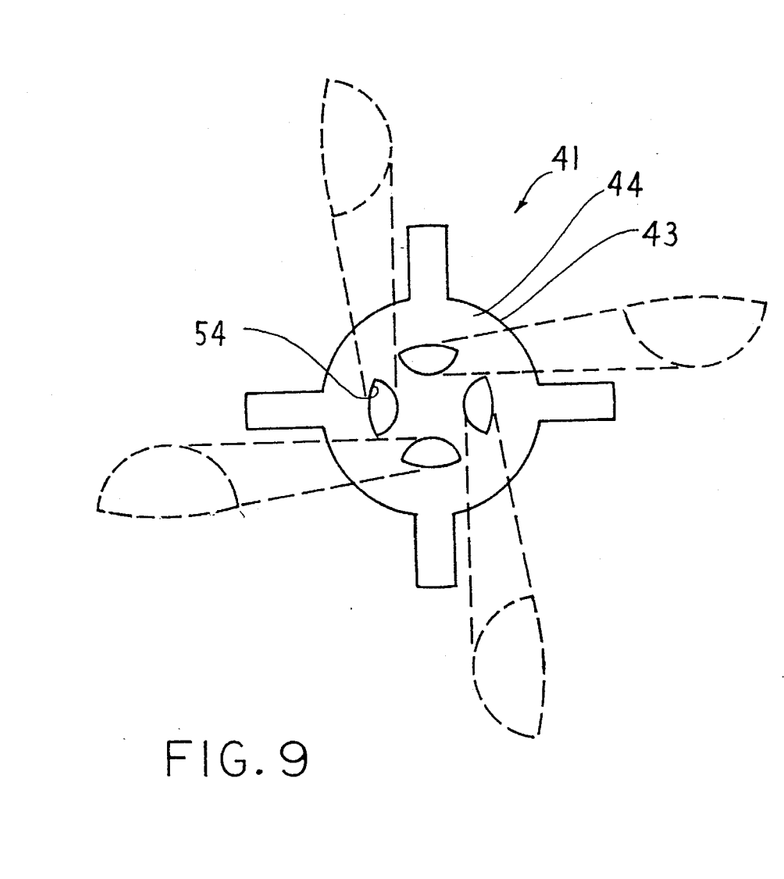
FIG. 9 is a schematic version of FIG. 5, showing the FIG. 2 liquid outflow pattern.

As irrigation liquid flows forward (see arrow A2, A3 and A4 in FIG. 6) through the tip member 41, it is angled radially outward by the nose 57 of the core 52 and circumferentially by the spiraling passages 54. Irrigation liquid then passes forwardly and somewhat circumferentially skewedly out of the passages 54. The sharp perimeter 67 and radially flat, distal end wall 44 of the tip member 41 provides for clean flow separation from the tip member 41 as irrigation liquid flow continues forwardly therebeyond, allowing only a few degrees of spread within each of the four exiting irrigation streams as indicated schematically in FIG. 2. The result is that such streams have length axes which are skewed with respect to each other, so as to cross each other in laterally spaced relation. Such streams angle away from the central axis of the irrigation tube. Such angled, pulsed streams can more easily be directed at an acute angle to a surgical site surface without having to angle the irrigation tube and handpiece. Such angled, pulsed streams also can dislodge debris from a surgical site surface by a kind of chiseling action, i.e. by digging laterally under debris and prying it off the surgical site surface as schematically shown in FIG. 9. Such skewed irrigation liquid stream squirts forward from the distal end of the suction tube 22, as generally indicated by the arrow A5 in FIG. 2, at an included angle slightly less than required to clear the lip 35 of the spray shield 30, in case the apparatus is being used with such a spray shield.

A pulsed flow of irrigation liquid forward from the wand 20 is very schematically indicated by longitudinal segmenting of the streams in FIG. 2. The pulsed irrigation liquid thus tends to be forwardly projected from the tip member 41 as four skewed series of axially discrete slugs, though of course with shape less sharply defined than schematically shown in FIG. 2. A series of liquid pulses, projected forwardly and circumferentially skewedly from the circumferentially spaced forward ends of the passages 54, thus appears as four circumferentially separate pulse streams, generally as schematically indicated in FIG. 2.

The passages 54 are intentionally of large cross section, to restrict irrigation flow forwardly therethrough as little as possible. As seen for example in FIG. 5, the minimum circumferential spacing between adjacent passages 54 is less than the radial extent and less than half the circumferential extent of the cross section of the passages 54. Further, as seen in FIG. 6, the passages 54 extend radially outward to the inner surface of the bore 73 of the irrigation tube 23. Both these features increase the total flow cross section of four passages 54 relative to that of the bore 73 of the irrigation tube 23, so as to minimize flow restriction by the passages 54. Separation of the flow into the flow passages 54 is needed to provide a rigid support for the core 52 centrally of the tip member 41. Thus, although the core 52 is rigidly supported with respect to the irrigation tube 23, the flow cross section area through the tip member 41 is as large as possible a fraction of the flow cross section within the irrigation tube 23.

While the apparatus shown, including the tip member 41, is usable for a variety of surgical jobs, it is particularly useful in knee replacements where it is necessary to clean the bone before installing the implant. To this end, the tip member 41 provides a forceful precisely directable stream (in the embodiment shown a pulsed stream) of irrigation liquid against the surface SU of the surgical site. As seen in FIG. 2, the irrigation liquid stream LS is skewed with respect to the central longitudinal axis of the tubes 22 and 23 (and indeed with respect to the three other liquid streams produced by this tip member). In other words, the stream LS leaves the tip member at the central plane thereof in FIG. 2 and proceeds downwardly and rightwardly past the right side of the tip member and suction tube 22 to impinge on the surgical site surface SU. The stream LS thus hits the surgical site surface SU at a sharper angle (smaller acute angle) than it would otherwise do, while yet being free of interference with the suction tube and spray shield 30 (FIG. 1), if provided with a spray shield. By striking the surgical site surface SU at a relatively sharp angle (relatively small acute angle) the forceful liquid stream, particularly when pulsed, tends to chisel under bits of soft tissue clinging to the surface of the bone at the surgical site surface and thereby more easily pry such soft tissue off the surface of the bone, rather in the manner of a carpenter's pry bar, a paint removing putty knife or a woodworking chisel. Indeed, in the embodiment shown, four such pulsed streams LS simultaneously can act on the surgical site surface SU to remove therefrom unwanted bits B (FIG. 2) of soft tissue.

It is contemplated that this array of streams, particularly pulsed streams, LS can be used in other surgical site configurations, for example for cleaning unwanted soft tissue from bone surface in a narrow channel or opening, such as the central channel of the femur preparatory to a hip joint replacement.

A stream, or pulsed liquid stream, emerging coaxially from the irrigation tube 23 absent the tip member 41, normally could not be angled with respect to the surface SU of the FIG. 2 surgical site without angling the handpiece in its entirety. Even then, only one stream would be available and only one portion of the surgical site surface SU could be cleaned at a given time. The present invention avoids the need to tilt the handpiece with respect to the surgical site surface SU, quadruples the number of streams of liquid simultaneously available for cleaning, spaces the streams LS so they do not interfere with each other upon impact with the surgical site surface SU, and provides the streams LS at a good effective cleaning angle automatically when the handpiece is held with its irrigation and suction tubes 22 and 23 substantially perpendicular to the surgical site surface SU.

The direction of the streams LS is controlled by the direction of the passages 54 in the tip member 41. In particular, the tip member cooperates with the inside surface of the irrigation tube 42 to determine the direction and cross section of the streams LS as well as to minimize the flare, or divergence, of liquid within each stream.

The rounded nose 57 helps to angle radially outwardly, into the rear ends of the passages 54, the central core of the irrigation liquid flow in the irrigation tube 23. The lands 56, at their rear ends, circumferentially separate the irrigation flow into the four passages 54. The outer, annular portion of the forward irrigation flow from the irrigation tube 23 continues its forward flow along the interior surface of the irrigation tube 23 into and along the passages 54, since the radially outer surface of the passages 54 is the inner surface of the irrigation tube 23 almost throughout the entire length of the tubular member 41. The quarter turn spiralling of the passages 54 also imparts some skewing, or sideward component, to the primarily forward motion of the liquid flow. Thus, it will be seen that the momentum of liquid flowing forward the length of the irrigation tube 23 is disturbed as little as possible in dividing it into the four somewhat sidewardly skewed streams LS (FIG. 2).

Although the tip member 41 is recessed somewhat with respect to the forward end of the suction tube 22, to a point just behind the notches 27 therein, the angle of the liquid streams LS do not diverge so far as to interfere with the forward end portion 32 of the suction tube 22 (nor with, as above mentioned, the spray shield 30 if one is used).

If the liquid streams LS were simply angled radially outward away from the central axis of the irrigation tube 23 and away from each other as well, the streams would tend to interfere with the forward end of the suction tube 22 as well as with the spray shield 30 (where one is used), were the streams LS angled to strike the surface SU in FIG. 2 at the relatively sharp angle shown. The skewing of the streams LS in the manner shown in FIG. 2, due to the relative skewing of the passages 54 with respect to each other, avoids this problem and still provides the relatively sharp angle of attack of the streams against the opposing surgical site surface SU in FIG. 2.

The tip 41 is preferably of relatively rigid, molded plastics material, such as molded acrylic.

Diametrically spaced ones of the irrigation liquid streams are essentially skewed with respect to each other in the region of the distal end wall 44 of the tip member 41, as generally indicated in FIGS. 2 and 9. The skewed orientation of the irrigation flow streams emerging from the tip member 41 also tends to impart something of the circumferential swirling movement to irrigation liquid and dislodged debris pooled at the surgical site surface SU, as indicated by the arrow CS.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A surgical irrigation wand for a surgical irrigation handpiece, comprising:

means defining a surgical irrigation tube for connection to an irrigation liquid outlet of a surgical irrigation handpiece, said tube having a distal end for directing irrigation liquid flow forwardly toward a surgical site; and tip means fixed adjacent said distal end of said tube for shaping said flow and projecting multiple, narrow, discrete streams of irrigation liquid forwardly from said tube, which streams have length axes which are skewed with respect to each other, so as to cross each other in laterally spaced relation, which streams angle away from the central axis of said irrigation tube and forwardly from a distal end of said tip means to corresponding circumferentially spaced points on the perimeter of an imaginary circle, rather than the center of such circle, spaced forwardly from said tip means on the surgical site for wetting said circumferentially spaced points at a given instant, said tip means having a forward facing surface proximate said distal end thereof and perforated by multiple discharge apertures from which said streams project, said discharge apertures being spaced one from the other, said tip means including means for forwardly diverging said flow of irrigation liquid to said apertures, said means for diverging said flow comprising a core extending rearwardly from said forward facing surface and having a rearwardly tapered portion.

2. A surgical irrigation wand for a surgical irrigation handpiece, comprising:

means defining a surgical irrigation tube for connection to an irrigation liquid outlet of a surgical irrigation handpiece, said tube having a distal end for directing irrigation liquid flow forwardly toward a surgical site;

tip means fixed adjacent said distal end of said tube for shaping said flow into multiple, narrow, discrete streams of irrigation liquid, which streams have length axes which are skewed with respect to each other, so as to cross each other in laterally spaced relation, which streams angle away from the central axis of said irrigation tube and thereby for wetting corresponding circumferentially spaced points on the perimeter of a circle, rather than the center of such circle, on the surgical site at a given instant, said tip means comprising an elongate body having:
(i) an outer perimeter surface;
(ii) a distal end wall;
(iii) a proximal end having an annular, coaxial, proximally opening recess for receiving said irrigation tube distal end;
(iv) a central, coaxial core having a tapered, generally conical rear end portion offset rearward from said distal end wall for forwardly diverging the flow of irrigation liquid therealong, said core being rearwardly fixedly cantilevered from said distal end wall and disposed coaxially with said proximally opening recess; and
(v) an array of plural, circumferentially spaced passages spiraling generally axially and circumferentially along said core and through said distal end wall for channeling the diverged flow of irrigation liquid skewedly through said distal end wall, said array coaxially surrounding said core, said passages defining grooves in the perimeter surface of said core, said core having a proximal portion ungrooved by said passages, said grooves being separated circumferentially by lands.

3. The apparatus of claim 2 in which said annular recess extends substantially the length of said body and is sized to snugly receive therein the distal end of said irrigation tube, said tip means slightly overhanging forwardly from said irrigation tube, said irrigation tube having an interior surface close adjacent the radially outer surface of said lands and serving as the radially outer wall of said passages, said grooves radially opposing said irrigation tube interior surface, such that a radially outer portion of the liquid flow in said irrigation tube can pass straight forward undeflected into said passages.

4. The apparatus of claim 3 including means defining a suction tube for connection to a suction port of a surgical irrigation handpiece, said suction tube substantially coaxially surrounding said irrigation tube, plural circumferentially spaced fins extending along and radially out from said outer perimeter surface of said body, said fins being substantially rectangular in a longitudinal/radial plane, said fins being substantially equal in radial extent to center said body and irrigation tube in said suction tube, said fins extending substantially the length of said body and contacting said suction tube at least at the ends of said fins for steadying said body and irrigation tube in said suction tube.

5. The apparatus of claim 2 including surface means in said body and formed by said core and passages for diverging the skewed irrigation liquid streams forwardly beyond said tip means toward a surgical site.

6. The apparatus of claim 5 including a substantially funnel-shaped spray shield extending forwardly beyond said irrigation tube and having a proximal collar portion sleeved on said distal end of said irrigation tube and having a wide distal mouth placeable close to a surface of a surgical site to limit sideward splashing of liquid from the surgical site during irrigation thereof, the included angle of said spray shield exceeding the included angle of divergence of irrigation flow forward from said tip means to avoid interference of the spray shield with irrigation liquid flow from said tip means to a surgical site, said skewed streams having a sharper acute angle of incidence on a radial plane at the surgical site than would nonskewed streams whose included angle of divergence would avoid interference with said spray shield.

7. The apparatus of claim 5 in which said surface means includes a rounded nose rearward extension of said core fixedly and coaxially extending rearward from the proximal end of said body.

8. A surgical irrigation handpiece unit, comprising:

a handpiece including means for forwardly projecting irrigation liquid forcibly toward a site on a patient to be treated;

means defining a wand including an irrigation liquid tube projecting forwardly from said handpiece toward the site on the patient;

tip means fixed adjacent a distal end of said tube for shaping irrigation liquid flow through the tube and projecting multiple, narrow, discrete streams of irrigation liquid forwardly from said tube, which streams have length axes which are skewed with respect to each other, so as to cross each other in laterally spaced relation, which streams angle away from the central axis of said irrigation tube and forwardly from a distal end of said tip means to corresponding circumferentially spaced points on the perimeter of an imaginary circle, rather than the center of such circle, spaced forwardly from said tip means on the site on the patient to be treated for wetting said circumferentially spaced points, said tip means having a forward facing surface proximate said distal end thereof and perforated by multiple discharge orifices from which said streams project, said discharge apertures being spaced one from the other, said tip means including means for forwardly diverging the flow of irrigation liquid to said apertures, said means for diverging the flow comprising a core extending rearwardly from said forward facing surface and having a rearwardly tapered portion, and said tip means further including passages extending rearwardly from said apertures into the vicinity of said tapered portion.

9. A surgical irrigation handpiece unit, comprising:

a handpiece including means for forwardly projecting irrigation liquid forcibly toward a site on a patient to be treated;

means defining a wand including an irrigation liquid tube projecting forwardly from said handpiece toward a site on a patient;

tip means fixed adjacent a distal end of said tube for shaping irrigation liquid flow through the tube into multiple, narrow, discrete streams of irrigation liquid, which streams have length axes which are skewed with respect to each other, so as to cross each other in laterally spaced relation, which streams angle away from the central axis of said irrigation tube and thereby for wetting corresponding circumferentially spaced points on the perimeter of a circle, rather than the center of such circle, on a site on a patient to be treated, said tip means comprising an elongate body having:
(i) an outer perimeter surface;
(ii) a distal end wall;
(iii) a proximal end having an annular, coaxial, proximally opening recess for receiving said irrigation tube distal end;
(iv) a central, coaxial core having a tapered, generally conical rear end portion offset rearward from said distal end wall for forwardly diverging the flow of irrigation liquid therealong, said core being rearwardly fixedly cantilevered from said distal end wall and disposed coaxially with said proximally opening recess; and
(v) an array of plural, circumferentially spaced passages spiraling generally axially and circumferentially along said core and through said distal end wall for channeling the diverged flow of irrigation liquid skewedly through said distal end wall, said array coaxially surrounding said core, said passages defining grooves in the perimeter surface of said core, said core having a proximal portion ungrooved by said passages, said grooves being separated circumferentially by lands.

10. The apparatus of claim 9 in which said annular recess extends substantially the length of said body and is sized to snugly receive therein the distal end of said irrigation tube, said tip means slightly overhanging forwardly from said irrigation tube, said irrigation tube having an interior surface close adjacent the radially outer surface of said lands and serving as the radially outer wall of said passages, said grooves radially opposing said irrigation tube interior surface, such that a radially outer portion of the liquid flow in said irrigation tube can pass straight forward undeflected into said passages.

11. The apparatus of claim 10 including means defining a suction tube for connection to a suction port of a surgical irrigation handpiece, said suction tube substantially coaxially surrounding said irrigation tube, plural circumferentially spaced fins extending along and radially out from said outer perimeter surface of said body, said fins being substantially rectangular in a longitudinal/radial plane, said fins being substantially equal in radial extent to center said body and irrigation tube in said suction tube, said fins extending substantially the length of said body and contacting said suction tube at least at the ends of said fins for steadying said body and irrigation tube in said suction tube.

12. The apparatus of claim 9 including surface means in said body and formed by with said core and passages for diverging the skew of irrigation liquid streams forwardly beyond said tip means toward a surgical site.

13. The apparatus of claim 12 including a substantially funnel-shaped spray shield extending forwardly beyond said irrigation tube and having a proximal collar portion sleeved on said distal end of said irrigation tube and having a wide distal mouth placeable close to a surface of a surgical site to limit sideward splashing of liquid from the surgical site during irrigation thereof, the included angle of said spray shield exceeding the included angle of divergence of irrigation flow forward from said tip means to avoid interference of the spray shield with irrigation liquid flow from said tip means to a surgical site, said skewed streams having a sharper acute angle of incidence on a radial plane at the surgical site than would nonskewed streams whose included angle of divergence would avoid interference with said spray shield.

14. The apparatus of claim 12 in which said surface means includes a rounded nose rearward extension of said core fixedly and coaxially extending rearward from the proximal end of said body.

15. A surgical irrigation tip member for fixing to an outlet distal end of an irrigation tube of a surgical irrigation handpiece wand for shaping irrigation flow into multiple, narrow, discrete streams of irrigation liquid and thereby for wetting corresponding circumferentially spaced points on the perimeter of a circle, rather than the center of such circle, on a patient site to be treated, said tip member comprising:

an elongate body having;

an outer perimeter surface;

a distal end wall;

a proximal end having an annular, coaxial, proximally opening recess for receiving an irrigation tube distal end;

a central, coaxial core having a tapered, generally conical rear end portion offset rearward from said distal end wall for forwardly diverging the flow of irrigation liquid therealong, said core being rearwardly fixedly cantilevered from said distal end wall and disposed coaxially with said proximally opening recess; and an array of plural, circumferentially spaced passages spiraling generally axially and circumferentially along said core and through said distal end wall for channeling the diverged flow of irrigation liquid skewedly through said distal end wall, said array coaxially surrounding said core, said passages defining grooves in the perimeter surface of said core, said core having a proximal nose ungrooved by said passages, said grooves being separated circumferentially by lands.

16. The apparatus of claim 15 in which said annular recess extends substantially the length of said body and is sized to snugly receive therein a distal end of an irrigation tube, the tip member slightly overhanging forwardly from an irrigation tube.

17. The apparatus of claim 16 including plural circumferentially spaced fins extending along and radially out from said outer perimeter surface of said body, said fins being substantially rectangular in a longitudinal/radial plane, said fins being substantially equal in radial extent to center said body and an irrigation tube in a surrounding suction tube of a surgical irrigation handpiece wand, said fins extending substantially the length of said body and adapted to contact a suction tube at least at the ends of said fins for steadying said body and an irrigation tube in such suction tube.

18. The apparatus of claim 15 including surface means in said body and formed by said core and passages for diverging the skewed irrigation liquid streams forwardly beyond the tip member toward a surgical site.

19. The apparatus of claim 18 in which said surface means includes a rounded nose rearward extension of said core fixedly and coaxially extending rearward from the proximal end of said body.

20. A surgical irrigation wand for a surgical irrigation handpiece, comprising:

means defining a surgical irrigation tube for connection to an irrigation liquid outlet of a surgical irrigation handpiece, said tube having a distal end for directing irrigation liquid flow forwardly toward a surgical site;

tip means fixed adjacent said distal end of said tube for shaping said flow forwardly toward a surgical site, said tip means comprising an elongate body having:

an outer perimeter surface;

a distal end wall;

a proximal end having an annual, coaxial, proximally opening recess for receiving irrigation liquid from said irrigation tube distal end;

a central, coaxial core having a tapered, generally conical rear end portion offset rearward from said distal end wall for forwardly diverging the flow of irrigation liquid therealong, said core being rearwardly fixedly cantilevered from said distal end wall and disposed coaxially with said proximally opening recess; and an array of plural, circumferentially spaced passages spiraling generally axially and circumferentially along said core and through said distal end wall for channeling the diverged flow of irrigation liquid skewedly through said distal end wall, said array coaxially surrounding said core, said passages defining grooves in the perimeter surface of said core, said conical core having a proximal nose ungrooved by said passages, said grooves being separated by lands.

21. The apparatus of claim 20 including surface means in said body and formed by said core and passages for diverging the skewed irrigation liquid streams forwardly beyond said tip means toward a surgical site.

22. The apparatus of claim 21 in which said flow diverging surface means includes a rounded nose rearward extension of said core fixedly and coaxially extending rearward from the proximal end of said body.

* * * * *